(12) United States Patent
Jugl et al.

(10) Patent No.: US 11,224,690 B2
(45) Date of Patent: Jan. 18, 2022

(54) FLEXIBLE CONTAINER FOR AN INJECTION DEVICE

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE); Stefan Blancke, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 552 days.

(21) Appl. No.: 15/568,114

(22) PCT Filed: Apr. 27, 2016

(86) PCT No.: PCT/EP2016/059423
§ 371 (c)(1),
(2) Date: Oct. 20, 2017

(87) PCT Pub. No.: WO2016/174099
PCT Pub. Date: Nov. 3, 2016

(65) Prior Publication Data
US 2018/0117244 A1    May 3, 2018

(30) Foreign Application Priority Data

Apr. 28, 2015 (EP) ..................... 15165376

(51) Int. Cl.
*A61M 5/152* (2006.01)
*A61M 5/148* (2006.01)
(Continued)

(52) U.S. Cl.
CPC ............ *A61M 5/152* (2013.01); *A61J 1/1406* (2013.01); *A61J 1/201* (2015.05); *A61M 5/148* (2013.01);
(Continued)

(58) Field of Classification Search
CPC .............. A61M 5/152; A61M 5/148; A61M 2005/14506; A61J 1/201; A61J 1/067; A61J 1/22
See application file for complete search history.

(56) References Cited

U.S. PATENT DOCUMENTS 4,337,769 A * 7/1982 Olson .................. A61M 39/22
                                                    604/251
5,342,313 A   8/1994 Campbell et al.
(Continued)

FOREIGN PATENT DOCUMENTS

EP      0722745 A1 * 7/1996 ............ A61M 5/152
WO      WO 89/11303      11/1989
(Continued)

OTHER PUBLICATIONS

International Search Report and Written Opinion in International Application No. PCT/EP2016/059423, dated , pages.
(Continued)

*Primary Examiner* — Catharine L Anderson
*Assistant Examiner* — Arjuna P Chatrathi
(74) *Attorney, Agent, or Firm* — Fish & Richardson P.C.

(57) ABSTRACT

The present disclosure relates to a flexible container for an injection device including a flexible bag having an interior volume to be filled with a liquid medicament, an outlet located at a first end of the bag, and a contraction member connected to the bag to displace a second end of the bag located opposite to the first end towards the first end.

15 Claims, 1 Drawing Sheet

(51) Int. Cl.
  *A61J 1/20* (2006.01)
  *A61J 1/14* (2006.01)
  *A61J 1/06* (2006.01)
  *A61M 5/145* (2006.01)

(52) U.S. Cl.
  CPC ..... *A61J 1/067* (2013.01); *A61M 2005/14506* (2013.01)

(56) References Cited

U.S. PATENT DOCUMENTS

| | | | |
|---|---|---|---|
| 5,628,308 A * | 5/1997 | Harges, Jr. | A41D 13/1153 128/201.25 |
| 6,251,098 B1 | 6/2001 | Rake et al. | |
| 2005/0277882 A1 * | 12/2005 | Kriesel | A61M 5/14244 604/131 |
| 2008/0319385 A1 * | 12/2008 | Kriesel | A61M 5/148 604/88 |
| 2011/0034872 A1 * | 2/2011 | Chiravuri | A61M 5/14276 604/132 |
| 2012/0016306 A1 * | 1/2012 | Lee | A61M 5/152 604/153 |
| 2013/0180618 A1 * | 7/2013 | Py | A61J 1/1475 141/2 |

FOREIGN PATENT DOCUMENTS

| | | |
|---|---|---|
| WO | WO 2011/015912 | 2/2011 |
| WO | WO 2011/023632 | 3/2011 |
| WO | WO 2011/029828 | 3/2011 |

OTHER PUBLICATIONS

International Preliminary Report on Patentability in International Application No. PCT/EP2016/059423, dated Oct. 31, 2017, 6 pages.

* cited by examiner

FLEXIBLE CONTAINER FOR AN INJECTION DEVICE

CROSS REFERENCE TO RELATED APPLICATIONS

The present application is the national stage entry of International Patent Application No. PCT/EP2016/059423, filed on Apr. 27, 2016, and claims priority to Application No. EP 15165376.3, filed on Apr. 28, 2015, the disclosures of which are expressly incorporated herein in entirety by reference thereto.

TECHNICAL FIELD

The present disclosure relates to the field of flexible containers for injection devices comprising a flexible bag to be filled with a liquid medicament to be injected or delivered by the injection device.

BACKGROUND

Drug delivery devices for administering liquid medicaments are widely known in the art. Parenteral administering of liquid medicaments is typically conducted by means of injection devices, such like syringes, pen-type injectors or by means of infusion pumps, e.g. by way of micropumps.

For treatment of chronic diseases, such like diabetes the medicament has to be regularly administered according to a predefined schedule. Known drug delivery devices may either be adapted for discrete use for injecting of a predefined amount of the medicament a given number of times during the day. Alternatively, such drug delivery devices may be adapted for continuous or quasi-continuous delivery of the medicament through a permanent fluid connection between the delivery device and the patient. Continuous or constant administering of the medicament is typically conducted by means of infusion pumps that are relatively expensive.

Such drug delivery devices typically comprise a container or reservoir to accommodate the liquid medicament and having an outlet in fluid communication with some kind of infusion or injection needle. Moreover, such drug delivery devices also comprise a drive mechanism that is operable to expel or to withdraw a predefined amount of the liquid medicament from the container or reservoir and through the infusion or injection needle into biological tissue of the patient.

There exist reusable as well as disposable devices, wherein with reusable devices the medicament-containing reservoir or container is to be replaced when empty. With disposable drug delivery devices a pre-filled reservoir is non-detachably arranged in the device. When the medicament contained therein has been used up the entire device is intended to be discarded.

Traditionally, vitreous or glass cartridges have been widely used in injection or infusion systems to contain or to accommodate the liquid medicament, hence a particular pharmaceutical composition. Glass cartridges, vials or carpules provide a large degree of optical transparency and are substantially inert to the medicament. This means, that substantially no interaction between the medicament and the glass cartridge takes place even under long term storage conditions, i.e. when the medicament is stored and contained in the cartridge for time intervals of severely years.

Vitreous cartridges or glass cartridges are prone to mechanical impact and may therefore represent a concern for patients but as well for the pharmaceutical industry. Glass breakage typically represents a hazard for the patient as well as for the industrial production environment. Moreover, handling of broken glass is quite risky and dangerous for the persons concerned with a broken cartridge.

Especially with highly concentrated medicaments and with infusion pump applications comparatively small volumes have to be injected or low volume flow rates have to be realized. Extraction and withdrawal of a comparatively small amount of medicament from a vitreous cartridge may be rather elaborate since a piston typically sealing a proximal end of the cartridge is to be displaced in distal, hence in injection direction typically by means of a plunger of the drug delivery device. For such application scenarios use of a deformable or flexible container or reservoir would be advantageous. As the medicament is sucked or withdrawn from the interior of the container the container is subject to a modification of its geometric shape and may start to collapse.

With flexible containers or flexible bags containing a liquid medicament it is desirable to provide a complete emptying of the content of the container. Hence, a flexible container is collapsible as its content is withdrawn or expelled from the container. Some flexible containers used with injection devices comprise an outlet that may be penetrable by a piercing element. The outlet may comprise a pierceable seal, such like a septum that is to be pierced and intersected by a withdrawal device, typically in the form of a cannula or an injection needle penetrating the seal and gaining fluid transferring access to the interior of the flexible bag. Naturally, a tipped end of a cannula or injection needle is then located inside the interior of the flexible bag.

But as the flexible bag is subject to collapsing the tipped end of the cannula or injection needle located inside the flexible bag may harm the integrity of the flexible bag, in particular of a sidewall portion located opposite or adjacent to the outlet thereof. With a withdrawal or emptying of the container by way of suction a withdrawal mechanism, typically implemented by a suction pump, has to work against a potential mechanical resistivity of the container. Depending on the elasticity of the material the container is made of a substantial suction force may have to be provided in order to withdraw the medicament from the container.

SUMMARY

Certain aspects of the present disclosure provide an improved flexible container for an injection device, which flexible container is less prone to self-damaging during an emptying of the flexible container. Moreover, the flexible container certain aspects provide a controlled and well defined collapsing behavior as the liquid medicament is withdrawn or expelled therefrom. In some aspects, the container exhibits an excellent collapsing behavior. Furthermore, in some aspects, the flexible container is cost efficient to manufacture, especially in a mass-manufacturing process.

In a first aspect a flexible container for an injection device is provided. The flexible container comprises a flexible bag having an interior volume to be filled with a liquid medicament. The flexible container further comprises an outlet located at a first end of the bag. The flexible container further comprises a contraction member connected to the bag to displace a second end of the bag located opposite to the first end towards the first end. By means of the contraction member a well-defined collapsing behavior of the flexible bag is obtained as the liquid medicament is withdrawn from its interior volume. The contraction member may even support a contraction and collapsing of the flexible bag and may thus even exert a particular pressure towards the liquid medicament, so that the medicament may start to pour through the outlet as the outlet is in fluid communication with the environment. The bag is configured as a flexible bag so that every section or portion of the bag is flexible. In particular, at least one of the first end and the second end is flexible.

In a particular embodiment the outlet is implemented as a pierceable seal penetrable by a tipped cannula or the like piercing element. As soon as the outlet is pierced the contraction member may provide a constant flow of the liquid medicament therethrough due to a significant and permanent collapsing force exerted to the flexible bag. By means of the contraction member, the collapsing behavior of the flexible bag is controllable to a large degree.

The contraction member may be connected to the mutually oppositely located first and second ends of the flexible bag, thereby bringing together first and second ends in a well-defined way as the liquid medicament is withdrawn from the flexible bag.

Furthermore, the contraction member is contractible or collapsible into a rather compact and minimal geometric shape, which is large enough to prevent stitching or damaging of the second end by means of a piercing element penetrating the outlet or its seal. In this way the contraction member actually helps to prevent any self- and unintended damaging of the flexible bag.

According to an embodiment the contraction member is connected to a sidewall of the bag that is located between the first end and the second end. The sidewall of the bag may be integrally formed with at least one of the first end and the second end. The sidewall may be also integrally formed or integrally connected with both oppositely located ends. Hence, the sidewall and the two oppositely located ends of the bag may be constituted by one and the same flexible material, such like a flexible but fluid-impermeable foil.

Furthermore, the contraction member is located at a certain distance from the second end of the flexible bag. It is particularly conceivable that the distance between an end section of the contraction member and the second end of the bag is at least as large as a penetration depth of a piercing element inside the flexible bag. In this way, a piercing and a damaging of the flexible bag, in particular of its second end by means of the piercing element extending through the outlet and into the interior volume of the flexible bag can be effectively prevented. At least a risk of self-damaging can be substantially reduced.

According to a further embodiment the contraction member comprises a tension spring having at least two windings enclosing the bag. Typically, the tension spring comprises several windings extending around the sidewall of the bag. The tension spring may be of helical shaped. In particular, at least the oppositely located longitudinal ends of the tension spring are connected with correspondingly located sidewall portions of the flexible bag. In this way the contraction member exclusively serves to collapse, to shrink or to contract the sidewall of the bag. Further, at least one of first and second ends may remain substantially unaffected by the contraction of the contraction member.

According to another embodiment at least one end of the contraction member is located at a predetermined distance from at least one of the first and the second end of the flexible bag. In this way, the contraction member exclusively serves to shrink or to contract the sidewall of the bag while leaving at least one of its first or second ends substantially unaffected with regard to their respective geometry. The sidewall of the flexible bag is substantially of tubular shape. However, the sidewall of the flexible bag may comprise numerous different geometries and cross sections. It is conceivable, that the sidewall is of substantially cubic or rectangular or even quadratic shape. Then, the contraction member may be accordingly of rectangular or quadratic shape. It is generally intended that the outer shape of the flexible bag's sidewall corresponds with the overall geometry of the contraction member.

According to a further embodiment the contraction member comprises a metallic material, a plastic material or a combination thereof. The contraction member may comprise a spring steel. Alternatively, the contraction member and its elastic behavior may also be attained by a plastic material. It is even conceivable, that the contraction member comprises a metallic section and a plastic section. Alternatively or additionally it is conceivable, that the contraction member comprises a metallic core coated by or embedded in a plastic material. It is also conceivable that the contraction member comprises a fiber reinforced plastic material.

A conventional spring steel-based contraction member as well as an implementation in plastic is rather cost efficient and enables manufacturing of the flexible and collapsible container in a mass manufacturing environment.

According to a further embodiment the contraction member is connected to the flexible bag with at least two fixations that are separated from each other in an axial direction (z). Typically, the axial direction extends from the bag's first end towards the bag's second end. By contracting the flexible bag with its second end approaching the first end, its sidewall collapses in axial direction. In other words, the axial extension of the sidewall extending between the first end and the second end reduces under the action of the contraction member.

By means of at least two fixations the contraction member, in particular axially separated portions thereof are separately connectable to respective portions of the bag that are correspondingly separated in axial direction. In this way, the outer dimensions and shape of the flexible bag may change in unison with the overall dimensions and geometric shape of the contraction member.

In another embodiment the contraction member is connected to an outside facing portion of the flexible bag. In this way, the contraction member is not in contact with the liquid medicament located in the interior volume of the flexible bag. Connecting of the contraction member to an outside facing portion of the flexible bag, in particular to a sidewall of the flexible bag, leaves the liquid medicament located therein substantially unaffected.

In an alternative embodiment the contraction member is connected to an inside facing portion of the flexible bag. In this embodiment the contraction member comprises a material being substantially inert to the liquid medicament. Alternatively, the flexible bag comprises a hollow-shaped sidewall portion, in which hollow sidewall the contraction member is located. By having the contraction member arranged either in a hollow section of the flexible bag's sidewall or in the interior volume of the flexible bag the contraction member is effectively protected against any mechanical or environmental influences by the flexible bag itself. Moreover, the contraction member could even be hidden inside the flexible bag, namely when the flexible bag is at least partially opaque or non-transparent. In this way, the existence of the contraction member could be hidden to end consumers or users of the flexible container or of the injection device.

According to another embodiment the contraction member and the bag are adhesively attached. It is even conceivable, that the contraction member and the bag are mutually welded, e.g. by heat staking, ultrasonic welding or even by application of laser welding. For implementing a mutual welding of bag and contraction member it is beneficial, that both, the contraction member and the bag comprise a plastic, a thermoplastic or an elastomeric material or combinations thereof.

In a further embodiment, the flexible bag may comprise or may consist of at least one of the following materials: thermoplastic elastomers (TPE), silicon rubber, butadiene rubber (BR), styrene butadiene rubber (SBR), styrene-ethylene/butylene-styrene type polymers (SEBS), LDPE, LLDPE, ethylene vinyl acetate (EVA), random copolymers of VP, polybutene-1, COC- or COP-based elastomers. The flexible bag may further comprise a comparatively thin layer of polymeric material. Then it may comprise or consist of one of the following materials or combinations thereof: MDPE, high-density polyethylene (HDPE), PP, in form of homopolymer, random or heterophasic copolymers, polybutene-1, COC, COP, polymethylene pentane, PET, Polyethylenterephthalat Glycol (PET-G), PBT, PC, SAN or MABS.

In a further embodiment the flexible bag comprises a transparent portion or is made of a transparent material to allow visual inspection of its content.

According to a further embodiment the outlet of the flexible bag comprises a pierceable seal. Typically, the pierceable seal may be implemented like a septum known from pierceable cartridges of injection devices of pen-injector type. The piercable seal may comprise or consist of a natural or synthetic rubber, such like bromobutyl-rubber. The pierceable seal may be located in place at the first end of the bag, e.g. by means of a crimp cap. The pierceable seal is penetrable by a hollow cannula or by a correspondingly tipped injection needle. Via the pierceable seal of the outlet and by means of at least one piercing element penetrating therethrough the liquid medicament is withdrawable from the flexible bag.

In another embodiment the contraction member is contractible into a collapsed configuration, in which the contraction member comprises a minimum axial extension which is still larger than a maximum penetration depth of a piercing element penetrating the seal for withdrawal of the liquid medicament. In this way the contraction member actually prevents that the second end of the flexible bag located opposite to the first end it harmed or damaged by the tipped end of the piercing element extending through the outlet and reaching into the interior volume of the flexible bag.

According to a further embodiment the contraction member is pre-tensed in axial direction and is contractible in axial direction while substantially maintaining a constant cross-section in a plane perpendicular to the axial direction. This behavior of the contraction member is particularly attainable by means of a contraction member having a constant cross-section as seen in axial direction. By means of such a contraction member, at least one, typically both oppositely located first and second ends of the flexible bag may remain in an initial geometric shape.

In another embodiment of the flexible container at least one of the first end wall and the second end wall is seamlessly connected or is integrally formed with the sidewall. The flexible bag may comprise an integrally formed and substantially seamless structure in the region of the sidewall and in the region of both oppositely located ends.

It is conceivable that the flexible bag comprises only one annular or rectangular shaped seal surrounding the outlet or the pierceable seal thereof.

In another embodiment the outlet comprises a rigid socket connected to the flexible bag, e.g. by welding or by means of an adhesive. The rigid socket serves as a mount for the pierceable seal, typically made of a natural or synthetic rubber. The socket may comprise an injection molded plastic component or may comprise a metallic material, such like aluminum. The socket and the seal may provide or form a pierceable septum. Typically, it is the socket that is rigidly connected to the flexible bag and which intersects the end section or a sidewall of the flexible bag. The socket itself may be hollow or tubular shaped while the seal is arranged across an inner cross section of the socket.

The rigid socket may further provide a fastening or gripping structure to facilitate a well-defined handling of the bag and to provide a well-defined fastening of the flexible container inside a respective compartment of an injection device. The socket may further comprise a flange portion by way of which a fastening and overall handling thereof can be facilitated. The socket may be connected to the bag via a seam of the bag.

In a further embodiment the interior volume of the flexible container, hence the interior volume of the flexible bag is filled with the liquid medicament. Typically, the interior volume is filled bubble-free without any substantial entrapment or embedding of air. The total filling volume of the flexible container may be in a range of a few milliliters, such like at least 2 ml, 3 ml, 5 ml or 10 ml but less than 20 ml. Filling of the interior volume with the liquid medicament is obtainable without the necessity of providing a venting valve. Filling of the interior volume may be conducted against the action of the contraction member. Hence, in an unfilled configuration the contraction member may even prevent ingress of air into the interior volume. The contraction member therefore further supports a bubble-free filling of the interior volume with the liquid medicament. Also during emptying of the container the contraction member effectively prevents ingress of air and ingress of other substances or germs into the interior volume.

In a further embodiment, the seal, the socket and/or the flange portion thereof are located in a central area or central section of the first end. The seal, the socket and/or the flange portion may be located in a radial central area of the contraction member. Hence, the seal and the socket may be located at a predefined distance from the contraction member. Alternatively, it is also conceivable that the seal, the socket and/or the flange thereof is located at or inside the sidewall. Then, the seal and/or the socket and/or the flange thereof may be structurally connected to the contraction member, in particular to one or several windings of the contraction member. The seal may be located axially between two neighboring windings to provide unobstructed access to interior volume when piercing the seal with a piercing element, such like a cannula.

In another aspect the disclosure also relates to an injection device for withdrawing of a liquid medicament from a flexible container as described above. The injection device is typically configured to deliver the liquid medicament to biological tissue. This may take place in accordance to a variety of different ways. The injection device may be implemented as an auto-injector or as a peristaltic pump. The injection device may be equipped with a feeder assembly by way of which the liquid medicament can be withdrawn or sucked out of the flexible bag. However, by means of the contraction member the injection device does not necessarily require a feeder assembly. It is generally conceivable, that the contraction member serves to expel the liquid medicament from the flexible bag once the piercing element penetrates the outlet thereof.

According to a further embodiment the injection device has a pump in fluid connection with the flexible container. By means of a pump, the liquid medicament may be sucked from the flexible bag, wherein such a suction-based withdrawal supports and requires a collapsing and shrinking of the flexible bag in the course of liquid medicament withdrawal.

According to a further embodiment the flexible container is exchangeably arranged inside the injection device.

In the present context, the distal direction points in the direction of the dispensing end container, while the proximal end or proximal direction denotes the end of the container or a component thereof which is furthest away from the dispensing end.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH 2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\epsilon$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, an embodiment of the flexible container is described in detail by making reference to the drawings, in which.

DETAILED DESCRIPTION

Figure 1:
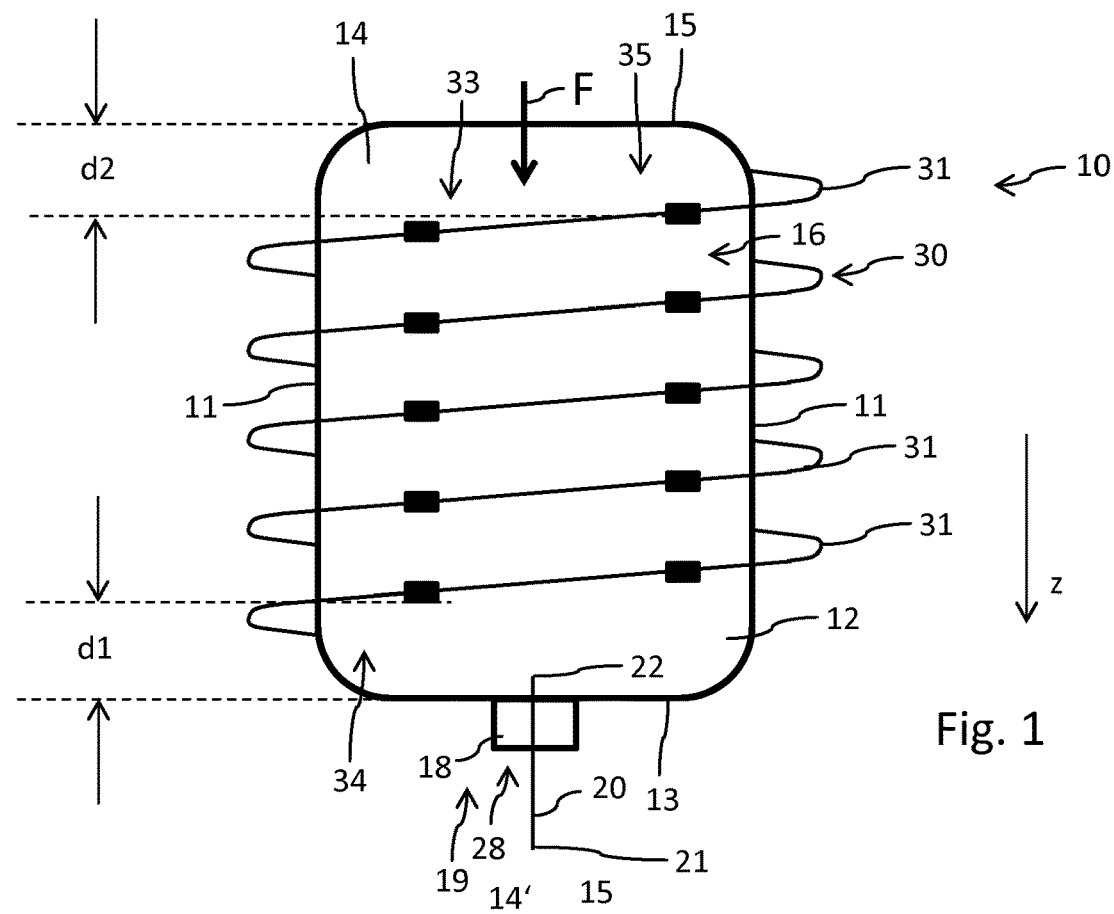
FIG. 1 schematically shows a side view of a flexible container equipped with a contraction member in an initial configuration.
Figure 3:
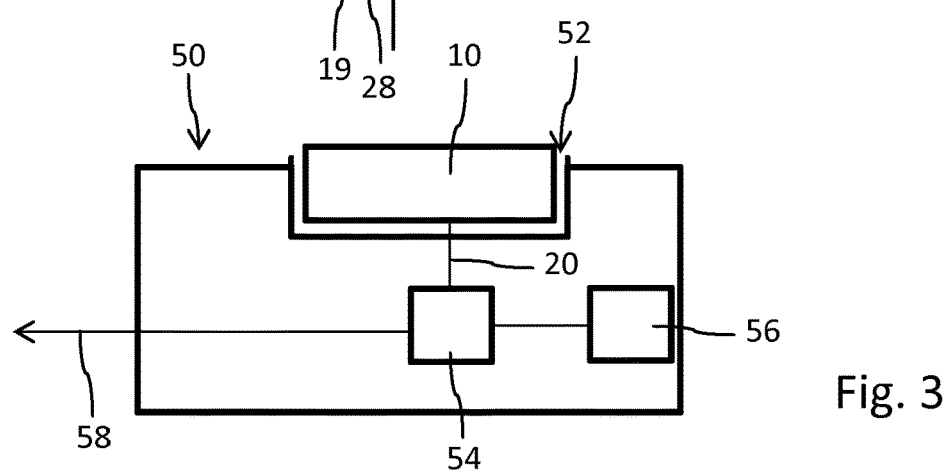

In FIG. 1 a flexible container 10 for an injection device 50 as schematically shown in FIG. 3 is illustrated. The container 10 comprises a flexible bag 12 having a first end 13 and an oppositely located second end 15. In the present illustration first and second ends 13, 15 are separated in or along an axial direction (z). The first end 13 is formed by a substantially planar-shaped bottom wall 13 while the second end 15 is formed by a correspondingly-shaped substantially planar top wall 15. Here, the terms 'bottom' and 'top' are only arbitrary and depend on the present orientation of the container 10. Moreover, the overall shape and geometry of first and second ends 13, 15 as well as of a sidewall 11 extending therebetween is rather arbitrary and may change in accordance with the demands of the container 10 and/or of a respective injection device 50.

Figure 2:
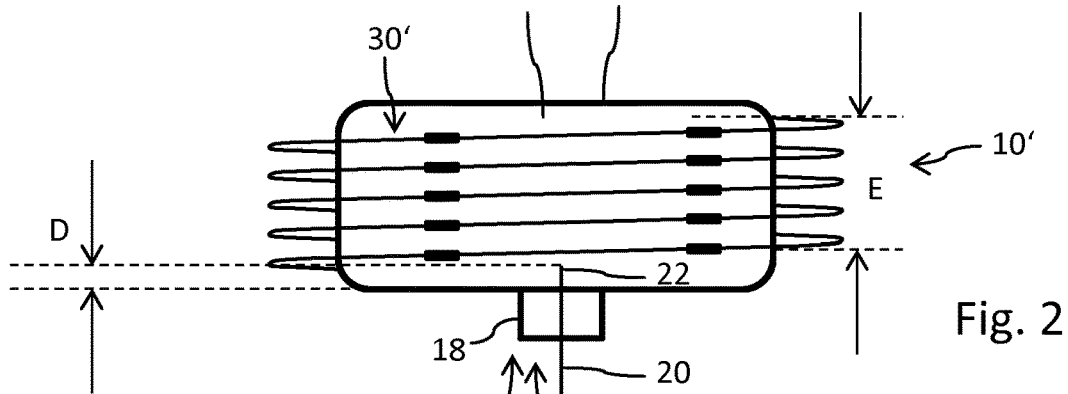
FIG. 2 shows the flexible container according to FIG. 1 in a collapsed state and FIG. 3 schematically illustrates an injection device having a pump and being further equipped with a flexible container according to FIG. 1.

The overall dimensions and the geometric shape of the flexible container 10 may vary with the geometric dimensions and shape of a compartment 52 of the injection device 50 that is adapted to accommodate such a flexible container 10. Only for a rather simple illustration of the working principle of the present disclosure the container 10 as shown in FIGS. 1 and 2 has a substantially tubular shape extending in axial direction (z). As it is apparent from FIGS. 1 and 2 first and second oppositely located ends 13, 15 of the flexible bag 12 are integrally formed and are mutually connected by a sidewall 11. The sidewall 11 may be of tubular shape but may also comprise a rectangular, triangular or oval cross-section perpendicular to the axial direction.

The interior 14 of the flexible bag 12 is filled with a liquid medicament 16. At its first end 13 the flexible bag 12 comprises an outlet 19. In the present embodiment the outlet 19 is provided with a pierceable seal 18 that is penetrable by a piercing element 20 of the injection device 50. The piercing element 20 comprises a distal end 21 that may be in fluid communication with a pump 56 and/or with an outlet 58 of the injection device 50. A proximal end 22 of the piercing element 20 is hence located in the interior 14. The piercing element 20 intersects the seal 18 of the outlet and enters the interior 14 of the flexible bag 12 by a predefined penetration depth (D) as indicated in FIG. 2. In order to avoid that the proximal end 22 of the piercing element 20 damages the sidewall 11 or the second end 15 of the flexible bag 12 as the flexible bag 12 collapses during withdrawal of the liquid medicament 16 the container 10 is equipped with a contraction member 30. The seal 18 is mechanically supported by a rigid socket 28 that may intersect the flexible bag. The rigid socket 28 may further comprise a radially outwardly extending flange portion. The socket 28 and/or the flange portion enable and facilitate gripping and the general handling of the flexible container. The socket 28 may provide a fastening structure for the flexible container to fasten and to fix the container inside a suitable compartment respective compartment 52 of the injection device 50.

Only as an example the contraction member 30 comprises several windings 31 extending along the outer circumference of the sidewall 11. The contraction member 30 comprises a tension spring 33 of substantially tubular or helical shape. Hence, the various windings 31 form a helix so that the tension spring 33 exerts a collapsing force F to the sidewall 11 and hence to the entire flexible bag 12. As further illustrated in FIG. 1 the contraction member 30 is connected with various fixations 32 to at least two sidewall sections of the flexible bag 12, which sidewall sections are separated in axial direction (z). In this way, the contraction member 30 is operable to shrink or to contract the sidewall 11 of the flexible bag 12 in axial direction (z). As further illustrated in FIG. 1, a distal end 34 of the contraction member 30 is located at a certain distance dl from the first end 13 of the flexible bag 12. In a similar way also a proximal end 35 of the contraction member 30 is located at a predefined axial distance d2 from the second end 15 of the flexible bag 12.

In this way it is effectively guaranteed that the first and second ends 13, 15 are kept separated by the contraction member 30 even when a collapsed state of the contraction member 30' as indicated in FIG. 2 has been reached. Moreover, the collapsed contraction member 30' as shown in FIG. 2 comprises a minimum axial extension (E) that is larger than the maximum penetration depth D of the piercing element 20. In this way it can be effectively prevented that the top wall or the second end 15 located opposite the piercing element 20 and hence opposite the outlet 19 is damaged or pierced by the proximal end 22 of the piercing element 20.

In addition to this self-damaging prevention the contraction member 30 also provides and induces a well-defined collapsing of the flexible bag 12. Due to several fixations 32 between the contraction member 30 and the sidewall 11 of the flexible bag 12 the flexible bag 12 and hence the collapsed container 10' maintains its overall cross section perpendicular to the axial direction or perpendicular to the contracting direction of the contraction member 30.

When assembled in the compartment 52 of the injection device 50 the piercing element 20 may be displaced and penetrated through the outlet 19 under the action of a piercing assembly 54. In addition, by means of a pressure pump or a suction pump 56 the liquid medicament 16 contained inside the container 10 can be withdrawn therefrom and can be further fed towards the outlet 58 of the injection deice 50. The device outlet 58 may comprise a tubing that terminates with a kind of piercing member by way of which the liquid medicament 16 is injectable into biological tissue of a patient.

LIST OF REFERENCE NUMBERS 10 container
11 sidewall
12 flexible bag
13 first end
14 interior volume
15 second end 16 liquid medicament
18 seal
19 outlet
20 piercing element
21 distal end
22 proximal end
28 socket
30 contraction member
31 winding
32 fixation
33 tension spring
34 distal end
35 proximal end
50 injection device
52 compartment
54 piercing assembly
56 pump
58 device outlet

The invention claimed is:

1. A flexible container for an injection device, comprising:
a flexible bag defining an interior volume configured to be filled with a liquid medicament, the interior volume being confined by:
 a first end of the flexible bag,
 a second end of the flexible bag, and
 a flexible sidewall located between the first end and the second end, the second end being opposite to the first end, and the second end being separated from the first end along a first direction,
an outlet located at the first end of the flexible bag,
a contraction member directly connected to an outside of the flexible bag and configured to displace the second end of the flexible bag towards the first end, wherein:
 the flexible sidewall comprises a first sidewall section and a second sidewall section separated from each other along the first direction,
 the contraction member is fixed to the first side wall section via a first fixation, and
 the contraction member is fixed to the second sidewall section via a second fixation.

2. The flexible container according to claim 1, wherein the contraction member comprises a helical shaped tension spring having at least two windings extending around the flexible bag.

3. The flexible container according to claim 1, wherein at least one end of the contraction member is located at a predetermined distance from the first end or the second end of the flexible bag.

4. The flexible container according to claim 1, wherein the contraction member comprises at least one of a metallic material and a plastic material.

5. The flexible container according to claim 1, wherein the contraction member is connected to the flexible bag via at least the first and second two fixations that are separated from each other in an axial direction.

6. The flexible container according to claim 1, wherein the contraction member is connected to an outside facing portion of the flexible bag.

7. The flexible container according to claim 1, wherein the outlet comprises a pierceable seal.

8. The flexible container according to claim 7, wherein the contraction member is contractible into a collapsed configuration, in which the contraction member defines a minimal axial extension, which is larger than a maximum penetration depth of a piercing element penetrating the pierceable seal.

9. The flexible container according to claim 1, wherein the contraction member is pre-tensed or biased in an axial direction and is contractible in the axial direction while substantially maintaining a constant cross-section in a plane perpendicular to the axial direction.

10. The flexible container according to claim 1, wherein at least one of the first end and the second end is seamlessly connected or integrally formed with the sidewall.

11. The flexible container according to claim 1, wherein the interior volume is filled with the liquid medicament.

12. An assembly comprising:
a flexible container comprising
 a flexible bag having an interior volume configured to be filled with a liquid medicament, the interior volume being confined by:
  a first end of the flexible bag,
  a second end of the flexible bag, and
  a flexible sidewall located between the first end and the second end, the second end being opposite to the first end and the second end being separated from the first end along a first direction,
 an outlet located at the first end of the flexible bag, and
 a contraction member directly connected to an outside of the flexible bag and configured to displace the second end of the flexible bag towards the first end; and
an injection device for withdrawing of a liquid medicament from the flexible container, the flexible container being attached to or located in the injection device, wherein:
 the flexible sidewall comprises a first sidewall section and a second sidewall section separated from each other along the first direction,
 the contraction member is fixed to the first side wall section via a first fixation, and
 the contraction member is fixed to the second sidewall section via a second fixture.

13. The assembly according to claim 12, comprising a pump in fluid communication with the flexible container.

14. The assembly according to claim 12, wherein the flexible container is exchangeably interconnectable with the injection device.

15. The assembly according to claim 12, wherein the interior volume is filled with the liquid medicament.

* * * * *